United States Patent [19]

Mausner et al.

[11] Patent Number: 4,690,785

[45] Date of Patent: Sep. 1, 1987

[54] LOW WATER NEUTRALIZATION TO PRODUCE A HIGHLY ACTIVE ALKARYL SULFONATE

[75] Inventors: Marvin L. Mausner, Teaneck, N.J.; Siegfried Meinstein, Oaklawn, Ill.

[73] Assignee: Witco Corporation, New York, N.Y.

[21] Appl. No.: 882,290

[22] Filed: Jul. 7, 1986

Related U.S. Application Data

[63] Continuation-in-part of Ser. No. 747,546, Jun. 21, 1985, abandoned, which is a continuation-in-part of Ser. No. 258,202, Apr. 27, 1981, abandoned.

[51] Int. Cl.$^4$ ............................................. C07C 143/24
[52] U.S. Cl. ............................................... 260/505 N
[58] Field of Search .................................... 260/505 N

[56] References Cited

U.S. PATENT DOCUMENTS 2,847,459  8/1958  Mitchell .............................. 260/505

*Primary Examiner*—Alan Siegel
*Attorney, Agent, or Firm*—Wallenstein, Wagner, Hattis, Strampel & Aubel, Ltd.

[57] ABSTRACT

An improved low water neutralization energy-saving process for the preparation of an alkaryl sulfonate by combining an alkaryl sulfonic acid with a salt-forming base, and utilizing the heat generated during the neutralization reaction to drive off the water present in the reaction mixture.

14 Claims, No Drawings

LOW WATER NEUTRALIZATION TO PRODUCE A HIGHLY ACTIVE ALKARYL SULFONATE

This application is a continuation-in-part application of application Ser. No. 747,546, filed June 21, 1985, now abandoned, which, in turn, is a continuation-in-part application of application Ser. No. 258,202, filed Apr. 27, 1981, now abandoned.

FIELD OF THE INVENTION

This invention relates to an energy saving process for the preparation of an alkaryl sulfonate. More specifically, this invention relates to the production of a dry alkylbenzene sulfonate prepared in a low water concentration system.

BACKGROUND OF THE INVENTION

The prior art discloses various methods for the preparation of alkaryl sulfonates, many of which involve the use of high percentages of water which must be eliminated in order to obtain a relatively dry product. As a result, they require high energy inputs and prolonged processing times to produce the desired end product, factors which contribute significantly to the cost of producing sulfonates by such methods.

U.S. Pat. No. 2,928,867, issued Mar. 15, 1960, to Kirk, et al, for example, discloses a method for preparation of stable alkaryl sulfonates. The method involves the use of alkaryl hydrocarbons such as dodecylbenzene to which is added sulfur trioxide. After cooling, a substantial quantity of water is then added, after which the solution is mixed and then neutralized with a 14% sodium hydroxide solution which, of course, increases the amount of water already in the reaction mixture.

U.S. Pat. No. 4,144,266, issued Mar. 13, 1979, to Plummer, et al, discloses a method for the sulfonation of crude oil to produce petroleum sulfonates by treating a crude oil with sulfur trioxide, removing unreacted hydrocarbons by the addition of water, and then neutralizing the formed sulfonic acid with a base.

U.S. Pat. No. 2,847,459, issued Aug. 12, 1959, to Mitchell, is directed to the preparation of aromatic sulfonate salts wherein a higher alkaryl substituted aromatic compound is first reacted with anhydrous sulfur trioxide. The resulting acid mix is then neutralized by pouring it into a vessel containing water and an alkali metal hydroxide. The slurry, containing the neutralized product, is "aged" at a temperature of approximately 65° C. to about 100° C. to provide a water-soluble alkayl aryl sulfonate having a substantially stable pH. Water comprises from 20% to 80% by weight of the mixture being aged.

U.S. Pat. No. 3,358,017, issued Dec. 12, 1967, to Seifert, relates to a process for producing substantially odorless alkaryl sulfonates by, in part, neutralizing an alkylaryl sulfonic acid with aqueous sodium hydroxide.

British Pat. No. 958,995, discloses a process for the preparation of alkyl-aryl sulfonates which involves first, sulfonating an alkyl-aryl compound, then neutralizing said compound with an aqueous solution of alkali metal hydroxide and cooling said neutralization mixture.

SUMMARY OF THE INVENTION

In accordance with the present invention, an essentially one-step process for the preparation of alkaryl sulfonates has been evolved which results in significant savings in energy and time over methods heretofore used to prepare such sulfonates. In addition to its energy and time saving features, the process enables more efficient use of equipment, and reduces the volume of materials and the types thereof heretofore required to produce alkaryl sulfonates. The process, in brief, comprises forming a reaction mixture consisting essentially of an alkaryl sulfonic acid and a salt-forming base; maintaining the reaction mixture at, or near, the exothermic temperature of the reaction between the acid and the base; and utilizing the heat generated during the neutralization reaction to remove water from the mixture to provide a dry, free-flowing powder. The entire process can be carried out in a single reaction vessel which, advantageously, is jacketed to enable the temperature of the reaction mixture to be controlled as desired. An anti-tack agent desirably is added to the reaction mixture to inhibit lumping or agglomeration of the powdered sulfonate during drying. The end product obtained by the process comprises at least 90% active material.

DETAILED DESCRIPTION OF THE INVENTION

The alkaryl sulfonic acids utilized in the practice of the present invention may be selected from a wide group. The generally optimum objectives of the invention, however, are attained with alkaryl sulfonic acids exemplified by alkylbenzene and alkyltoluene sulfonic acids wherein the alkyl substituent contains 10 to 18 carbon atoms. A preferred alkaryl sulfonic acid of this group is dodecylbenzene sulfonic acid.

The salt-forming bases employed in the process include alkali metal and alkaline earth metal hydroxides. Exemplary of such hydroxides are sodium, potassium and lithium hydroxide, and calcium and magnesium hydroxide. Especially preferred is sodium hyroxide. The salt-forming base can be used in solid form such as flakes, or chips, or in the form of an aqueous solution wherein the concentration of the base is at least about 50%, and preferably upwards of about 60% to about 70%, or higher.

The alkaryl sulfonic acid and the salt-forming base advantageously are intermixed in a jacketed reaction vessel provided with means for continuously mixing the reactants. In accordance with a preferred practice of the invention, the sulfonic acid is first introduced into the reaction vessel, and preheated to a temperature in the range of about 110° F. to about 200° F., preferably about 120° F. to about 150° F., by passing hot water or steam through the jacket of the reaction vesssel. The salt-forming base is then introduced into the vessel while continuously mixing the resulting reaction mixture. The mole ratio of alkaryl sulfonic acid to salt-forming base preferably is about 1:1. The weight ratio of acid to base employed may range from about 5:1 to about 8:1, provided that the acid-to-base mole ratios remain constant in order to complete neutralization of the sulfonic acid. An alternative procedure to stirring the salt-forming base into the sulfonic acid is to simultaneously spray the acid and the base into a jacketed reaction vessel.

Since the starting reaction mixture consists essentially of an alkaryl sulfonic acid and a salt-forming base in solid form, or as a concentrated aqueous solution, the quantity of water present in the reaction vessel following neutralization is low, usually below about 15%, by weight. The generally optimum objectives of the invention are achieved when the quantity of water present in the reaction vessel following neutralization is in the range of about 7% to about 12%, and, most desirably, in the range of about 8% to about 10%, by weight. As indicated hereinabove, the low concentration of water present in the reaction mixture enables the heat generated during the neutralization reaction to be utilized to drive off the water formed during the reaction. This unique feature of the process of the present invention has significant advantages both from the standpoint of reduction in energy input and reduction in processing time.

Generally speaking, the temperature of the reaction mixture during neutralization will be in the range of about 212° F. to about 240° F., or 250° F., depending, in the main, upon the concentration of the salt-forming base employed to neutralize alkaryl sulfonic acid. Thus, by way of illustration, where the salt-forming base comprises sodium hydroxide in the form of flakes, and the alkaryl sulfonic acid is dodecylbenzene sulfonic acid, the total concentration of water formed in the mixture will be of the order of about 7%, by weight, and the neutralization temperature will be in the range of about 240° F. to about 245° F. At that temperature range, the water formed during the neutralization reaction will be substantially completely removed to provide an end product in the form of a dry, free flowing powder. In those instances where the salt-forming base is in the form of a concentrated aqueous solution, the water formed in the reaction mixture will be in the range of about 9% to about 12%, by weight, and the neutralization temperature can range from about 212° F. to about 235° F. In such cases, it may be necessary, in order to provide a dry, free flowing end product, to apply heat for a short time to the jacketed reaction vessel to remove any residual water not driven-off by the heat generated during neutralization. Temperatures employed for this purpose can be range from about 210° F. to about 230° F., or higher.

The significant reduction in energy input realized with the process of the present invention over that of a process such as is disclosed in U.S. Pat. No. 2,847,459 to Mitchell is compellingly demonstrated by the following illustrations. If a dry product was to be prepared from an aqueous slurry containing 20% water obtained by the process of the Mitchell patent, 300% more energy would be required to remove the water from the slurry than would be required by the process of the present invention at the lower range, that is, 7% by weight water in the reaction mixture. The 300% figure, of course, is based upon the assumption that no water was removed from the reaction vessel by the heat of neutralization in accordance with the practice of the present invention. If that important aspect of the invention is taken into consideration, the 300% figure is of no significance since no energy input would be required to remove the water from the reaction mixture of the present process. If the reaction mixture contained 80% by weight water as disclosed in U.S. Pat. No. 2,847,459, the amount of energy required to provide a dry, free flowing product would be 1300% greater than the amount of energy required to produce a dry, free flowing product by the process of this invention at a 7% by weight water content. Again, the 1300% figure is based upon the assumption that no water is removed by the heat of neutralization as taught herein.

Following removal of the water from the reaction mixture, the dry product advantageously is cooled to room or ambient temperature by circulating water through the jacket of the reaction vessel, and is converted to powder form by the mechanical action of the reaction vessel. In order to prevent caking or lumping of the end product during drying, and to provide a free-flowing end product, an anti-tack, or anti-caking, agent desirably is added to the reaction mixture. Exemplary of anti-caking agents useful for this purpose are trisodium sulfosuccinate, and a mixture of sodium xylene sulfonate and trisodium sulfosuccinate. The quantity of anti-caking used can range from about 2% to about 5%, preferably about 2.5% to about 3%, by weight of the reaction mixture.

The resulting free flowing alkaryl sulfonate powder is at least about 90% active, or stated differently, comprises about 90% alkaryl sulfonate. When dissolved in water, the powdered product will have a pH of about 4.6 to about 11.5, usually about 7 or about 8.

The following examples are illustrative of the process of the present invention.

EXAMPLE 1

Equal molar proportions of dodecylbenzene sulfonic acid and sodium hydroxide in flake form are placed in a jacketed reaction vessel by first introducing the acid and heating it to a temperature of approximately 125° F. The sodium hydroxide is then slowly added to the acid with constant stirring over a period of about 25 minutes. The temperature of the exotherming reaction mixture is maintained at a temperature of approximately 235° F. by circulating tap water through the jacketed reaction vessel. The neutralization reaction is permitted to proceed until all of the water formed during neutralization has been removed by the heat of the reaction. The total time required to complete removal of the water is approximately 45 minutes. The final product is in the form of a dry, free flowing powder comprising about 90% dodecylbenzene sulfonate.

EXAMPLE 2

Dodecylbenzene sulfonic acid is added to a jacketed reaction vessel and heated to about 120° F. A 50° aqueous sodium hydroxide solution is slowly added with constant stirring to the sulfonic acid over a period of approximately 30 minutes. The molar proportion of the acid to the hydroxide in the vessel is approximately 1:1. The reaction mixture is permitted to exotherm while maintaining it at a temperature of approximately 230° F. by circulating tap water through the jacketed vessel. Trisodium sulfosuccinate is added to the vessel in an amount equal to approximately 2% by weight of the reaction mixture. The water in the mixture is progressively driven off as the neutralization reaction goes to completion. The final product is heated to a temperature of 240° F. for 20 minutes to remove any residual water. The dried product is in the form of a free flowing powder containing approximately 91% dodecylbenzene sulfonate.

While there has been disclosed and described a preferred embodiment of the invention, it should be understood that various changes and modifications may be made in the process without departing from the scope of the invention as defined in the appended claims.

What is claimed is:

1. A low water concentration, essentially one-step process for the preparation of an alkaryl sulfonate in the form of a dry, free flowing powder, comprising: forming a reaction mixture consisting essentially of an alkaryl sulfonic acid and a salt-forming base, the concentration of the salt-forming base in the mixture being such that the total concentration of the water in the reaction mixture which may be present in the salt-forming base and/or formed during the neutralization reaction between the alkaryl sulfonic acid and the salt-forming base will be below about 15%, by weight; and utilizing substantially only the heat generated during the neutralization reaction to remove the said water present in the salt-forming base and/or formed during said neutralization reaction from the mixture to provide a dry, free-flowing powder having an alkaryl sulfonate concentration of about 90%, by weight.

2. A process according to claim 1, wherein the alkaryl sulfonate is an alkylbenene sulfonate.

3. A process according to claim 2, wherein the alkaryl sulfonic acid is dodecylbenzene sulfonic acid.

4. A process according to claim 1, wherein the salt-forming base is in solid form.

5. A process according to claim 4 wherein the salt-forming base is sodium hydroxide in flake form.

6. A process according to claim 1 wherein the concentration of water in the reaction mixture is about 7% to about 12%, by weight.

7. A process according to claim 1 wherein a single reaction vessel is used to carry out the process.

8. A process according to claim 7 wherein a jacketed reaction vessel provided with mixing means is used.

9. A process according to claim 1 wherein the reaction mixture is formed by simultaneously spraying the sulfonic acid and the salt-forming base solution into a reaction vessel.

10. A process according to claim 1 wherein an anti-caking agent is incorporated into the reaction mixture.

11. A process according to claim 10 wherein the anti-caking agent is trisodium sulfosuccinate, or a mixture of sodium xylene sulfonate and trisodium sulfosuccinate.

12. A process according to claim 10 wherein the amount of anti-caking agent incorporated into the reaction mixture is about 2% to about 5% by weight of the mixture.

13. A process according to claim 1 wherein the reaction mixture is permitted to exotherm at a temperature of about 212° F. to about 250° F. until the water present in the reaction mxiture has been driven off.

14. A process according to claim 1 wherein heat is applied to the reaction mixture to remove any residual water not removed by the heat generated during the neutralization reaction.

* * * * *